US005556963A

United States Patent [19]

Liav et al.

[11] Patent Number: 5,556,963
[45] Date of Patent: Sep. 17, 1996

[54] SYNTHESIS OF 4-ALKOXY-N-ACETYLNEURAMINIC ACID

[75] Inventors: Avraham Liav, Denver, Colo.; Ragen F. Hardgrave, Cleveland, Tex.; Sheri Blystone, Concord, Ohio; Gregory A. Turner, Independence, Mo.

[73] Assignee: Oklahoma Medical Research Foundation, Oklahoma City, Okla.

[21] Appl. No.: 286,573

[22] Filed: Aug. 5, 1994

[51] Int. Cl.$^6$ ........................................ C07H 1/00
[52] U.S. Cl. .................. 536/55.3; 536/18.5; 536/18.6; 536/53
[58] Field of Search .................. 536/53, 55.3, 18.5, 536/18.6

[56] References Cited

U.S. PATENT DOCUMENTS

| | | | |
|---|---|---|---|
| 3,950,322 | 4/1976 | Thomas et al. | 536/17.2 |
| 5,138,044 | 8/1992 | Dasgupta | 536/18.5 |
| 5,191,073 | 3/1993 | Corey et al. | 536/17.2 |
| 5,239,091 | 8/1993 | Wong et al. | 549/419 |
| 5,252,458 | 10/1993 | Liav et al. | 435/5 |

FOREIGN PATENT DOCUMENTS

| | | | |
|---|---|---|---|
| 2062406 | 9/1992 | Canada. | |
| WO91/09972 | 7/1991 | WIPO | C12Q 1/34 |
| WO91/16320 | 10/1991 | WIPO | C07d 309/30 |
| WO92/06691 | 4/1992 | WIPO | C07D 309/28 |

OTHER PUBLICATIONS

Srivastava et al. *Carbohydr. Res.* 1993, 248, 167–178.
Jean–Marie Beau et al., "Synthèse De L'Acide 5–Acétamido–Didésoxy–4–O–Méthyl–N– Acétylneuraminique). Partie II", *Carbohydrate Research*, 67 (1978) pp. 65–77.
Jean–Marie Beau et al., "Synthèse De L'Acide 4–O–Méthyl–N–Acétylneuraminique. Partie I. Acétonation Du 3–Acétamido–3–Désoxy–D–glycéro–D–galacto –Heptose Diéthyldithioacétal", *Carbohydrate Research*, 65 (1978) pp. 1–10.
Richard Kuhn et al., "Überführung von 2–Amino–2-3–Desoxy–Hexosen Und–Pentosen", Bd. 636 (1960) pp. 164–173.
E. Zbiral et al, "Synthesis of the 4–Methylumbelliferyl 2α–Glycosides of 7–Epi, 8–Epi, and 7, 8–Bis(epi) –N–acetylneuraminic Acids, as well as of 7–Deoxy–, 8–Deoxy–, 9–Deoxy–, and 4, 7–Dideoxy–N_acetylneuraminic Acids and Their Behaviour Towards Sialidase from *Vibrio Cholerae*", *Liebigs Ann. Chem.*, (1989), pp. 519–526.
Warner et al., "Synthesis of 2'–(4–Methylumbelliferyl)–α–D–N–acetylneuraminic Acid and Detection of Skin Fibroblast Neuraminidase in Normal Humans and in Sialidosis", *Biochemistry*, vol. 18, No. 13, (1979), pp. 2783–2787.
Kim et al., "Enzymes in Carbohdyrate Synthesis: N–Acetylneuraminic Acid Catalyzed Reactions and Preparation of N–Acetyl–2–deoxy–D–neuraminic Acid Derivatives", *J. Am. Chem. Soc.*, (1988) 110, pp. 6481–6486.

Santer et al., "A Rapid Assay for Neurominidase—The Detection of Two Differences Associated With Virus Transformation", *Biochimica et Biophysica Acta*, 523 (1978) pp. 435–442.
Cabezas et al., "Neuraminidase From Influenza Virus (H3N2)—Specificity Towards Several Substrates and Procedure of Activity Determination", *Biochimica et Biophysica Acta*, 616 (1980) pp. 228–238.
Abstract #27461—Kiyotani et al., "Fluorometric Measurement of Neuraminidase Activity of Influenza Viruses", *Hiroshima J. Med. Sci.*, 33(2) (1984) pp. 287–292. (Listed in *Veterinary Science*.).
Abstract #78292—Kiyotani et al., "Enzymological heterogeneity of influenza B virus neuraminidase demonstrated by the *Science*, fluorometric assay method", *Zentralbl Bakteriol Mikrobiol Hyg Ser A*, 260(2): 273–285 (1985), pp. 273–285 (Listed in *Veterinary Biol. Abst* (81(8) AB 1090).
Abstract #117445—Takei et al., "Enzymologically Neuraminidase (NA) activity of 10 strains of influenza A and B viruses neuraminicases", *Virus* (Tokyo) (1986) 36(1): pp. 119–124. (*Veterinary Science*.).
Baumberger et al., "Deoxy–nitrosugars", *Helvetica Chimica Acta*, vol. 69 (1986), pp. 1535–1541.
Hagedorn et al., "Synthesis and Biological Properties of N–Acetyl–4–deoxy–D–neuraminic Acid", *Helvetica Chimica Acta*, vol. 69 (1986) pp. 2127–2133.
Baumberger et al., "4–Methylumbelliferyl 5–Acetamido–3, 4,5–trideoxy–α–D–manno–2–nonulopyranosidonic Acid: Synthesis and Resistance to Bacterial Sialidases", *Helvetica Chimica Acta*, vol. 69 (1986) pp. 1927–1935.
Brown et al., "Rapid Stereospecific Methylation of Alchohols and Glycols With Sodium Hydride/Methyl Iodide", *Communications*, pp. 434–435.
Gross et al., "Interaction of N–Acetyl–4–epi–D–neuraminic Acid with Key Enzymes of Sialic Acid Metabolism", *Biochemistry*, 1988, 27, pp. 4279–4283.
Liav et al., "Synthesis of 6–O–mycoloyl and 6–O–corynomycoloyl–α,αtrehalose", *Carbohydrate Research*, 125 (1984), pp. 323–328.
Pachucki et al., "Early Detection of Influenza Virus By Using a Fluorometric Assay of Infected Tissue Culture", *Journal of Clinical Microbiology*, Dec. 1988, pp. 2664–2666.

(List continued on next page.)

Primary Examiner—Gary L. Kunz
Assistant Examiner—Kathleen Kahler Fonda
Attorney, Agent, or Firm—Fitch, Even, Tabin & Flannery

[57] ABSTRACT

This invention relates to an improved process for the synthesis of 4-alkoxy-N-acetylneuraminic acids. According to the process of the invention, N-acetylneuraminic acid is first alkylated at C-1 and C-2 and then the vicinal hydroxyl groups at C-8 and C-9 are protected through the formation of a ketal. The resulting protected alkyl ester alkyl ketoside is then alkylated at the C-4 position whereby the hydrogen of the C-4 hydroxyl group is replaced with an alkyl group to form an alkoxy group. Deprotection is accomplished through the removal of the ketal group at C-8 and C-9 and removal of the alkyl groups at C-1 and C-2, thereby producing the 4-alkoxy-N-acetylneuraminic acid.

23 Claims, No Drawings

OTHER PUBLICATIONS

Yolken et al., "Fluormetric Assay for Measurement of Viral Neuramindase—Application to the Rapid Detection of Influenza Virus in Nasal Wash Specimens", *The Journal of Infectious Diseases*, vol. 142, No. 4, Oct. 1980, pp. 516–523.

Beau et al., "Metabolism of 4-O-Methyl-N-acetyl-neuraminic Acid a Synthetic Sialic Acid", *Eur. J. Biochem.*, 106 (1980), pp. 531–540.

Zbiral et al., "Strukurelle Abwandlungen an N-Acetyl-neuraminsuaren, 8[1] Synthese von 7-, 8-, 9-Desoxy-und 4,7-Didesocyneuraminsaure", *Monatshefte fur Chemie*, 199 (1988), pp. 127–141.

Myers et al., "The Synthesis of 4-Methylumbelliferyl α-Ketoside of N-Acetylneuraminic Acid and Its Use in a Fluormetric Assay of Neuraminidase", *Analytical Biochemistry*, 101, (1980) pp. 166–174.

SYNTHESIS OF 4-ALKOXY-N-ACETYLNEURAMINIC ACID

The present invention relates to an improved method for the synthesis of compounds useful in viral diagnostic assays. More particularly, the invention relates to an improved method for the synthesis of 4-alkoxy-N-acetylneuraminic acids.

BACKGROUND OF THE INVENTION

Infectious diseases are the single most common reason for physician office visits. Viruses are responsible for more of these infections than all other groups of microorganisms combined. Of all the various infections caused by viruses, the respiratory viruses (influenza A and B; parainfluenza 1, 2 and 3; respiratory syncytial virus; and adenovirus) are the most prevalent as a group. The lethality of the influenza virus was discovered in as early as 430 BC in the plague of Athens (Langmuir et al., *New Engl. J. Medicine*, 313 (1985) 1027). Influenza is the number one cause of acute respiratory illness and the fifth leading cause of death in the United States annually (*Morbidity Mortality Weekly Report*, 36 (1987) 2). As a result, the development of diagnostic methods for viruses and viral infections has become increasingly important.

The rapid diagnosis of viral infections has also become an integral part of good medical practice. Some viruses have definable antigens against which antibodies can be produced. Therefore, immunoassays have been widely used for the measurement of the presence of a virion. Where it is desirable to measure a broader group of virions, it may be possible to detect a particular component of the virus. For example, influenza viruses express surface glycoproteins having neuraminidase (sialidase) activity. The neuraminidase enzyme hydrolyzes substrates that contain 2-ketosidically linked N-acetylneuraminic acid (Neu5Ac, also known as sialic acid). Neu5Ac consists of a backbone of nine carbon atoms, a carboxyl group and an N-acetyl group. The general structure, as well as the numbering system used to denote the carbon atoms, is shown below.

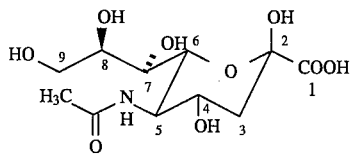

When a virion with neuraminidase activity is incubated with a chromogenic or fluorometric glycoside of Neu5Ac, the enzyme will cleave the chromogenic or fluorometric aglycon from the substrate, and the reaction product will indicate the presence of a virion.

One method for detecting the presence of a virus through the reaction of an enzyme with a chromogenic substrate for the enzyme is described in U.S. Pat. No. 5,252,458, which is incorporated herein by reference. An assay for the direct measurement of influenza neuraminidase was developed by Yolken et al., (*J. Infectious Diseases*, 142 (1980) 516–523). Yolken used the 4-methylumbelliferil-2-ketoside of Neu5Ac as a fluorescent substrate to measure neuraminidase activity in preparations containing small quantities of cultivated virus as well as in some nasal wash specimens from human volunteers infected with the influenza virus. Yolken suggested that "successful development of fluorometric enzyme assays for the detection of influenza neuraminidase might thus provide for a practical means of influenza diagnosis that is sufficiently rapid to allow for the institution of appropriate preventive and therapeutic interventions." According to Yolken, colorimetric assays were insufficiently sensitive for clinical applications. In contrast, Yolken noted that fluorometric assays might be suitable for detecting influenza neuraminidase in clinical samples.

Pachucki et al. (*J. Clinical Microbiology*, 26 (1988) 2664–2666) tested the 4-methylumbelliferyl-2-ketoside of Neu5Ac on clinical specimens collected from influenza patients. Due to its low sensitivity, the assay was not useful in detecting neuraminidase directly and rapidly in clinical specimens. The assay did, however, identify 91% virus-positive isolates 25 hours after inoculation of tissue cultures.

The use of modified Neu5Ac substrates can increase the specificity of the neuraminidase assay. In sialic acids, C-4 (see above structure) seems to play an important role in enzyme-substrate interactions. Further, since it is known that salivary bacterial enzymes exhibit neuraminidase activity (Varki et al., *J. Biol. Chem.*, 258 (1983) 12465–12471), it is essential to eliminate these undesired interactions. It has already been shown that ketosides of 4-methoxy-Neu5Ac are resistant towards bacterial sialidases, but are cleaved rapidly by viral sialidases (Beau et al., *Eur. J. Biochem.*, 106 (1980) 531–540).

The synthesis of 4-methoxy Neu5Ac has been described (Kuhn et al., *Liebigs Ann. Chem.*, 636 (1960) 164–173; Beau et al., *Carbohydr. Res.*, 65 (1978) 1–10; Beau et al., *Carbohydr. Res.*, 67 (1978) 65–77). However, the published procedure is not based on the direct alkylation of a suitably protected Neu5Ac derivative, and it involves many more steps. Also, because this method requires the use of hazardous substances such as hydrocyanic acid, it may not be commercially practical.

A direct methylation procedure is described in PCT publication WO 91/09972 (Jul. 11, 1991). According to this method, a methyl ester methyl ketoside of Neu5Ac (Neu5Ac-MEMK) is treated with tert-butyldimethylsilyl (TBMS) chloride, imidazole and a catalytic amount of 4-dimethylaminopyridine at 65° C. to afford 9-O-TBMS-Neu 5Ac-MEMK. Treatment of this compound with acetone and a catalytic amount of p-toluenesulfonic acid monohydrate at room temperature yields 9-O-TBMS-7,8-isopropylidene-Neu5Ac-MEMK, which is then treated with diazomethane/trifluoroborate in ether at 0° C. to give the corresponding 4-methoxy derivative. This compound is deprotected by treatment with tetrabutyl-ammonium fluoride in THF, followed by alkaline hydrolysis with sodium hydroxide and acid hydrolysis with dilute hydrochloric acid/Dowex 50 (H$^+$) to give 4-methoxy-N-acetylneuraminic acid. This method results in poor yields and requires the use of diazomethane, a gaseous reagent which is both toxic and explosive.

SUMMARY OF THE INVENTION

This invention offers a convenient and straightforward synthesis of 4-alkoxy-N-acetylneuraminic acid (4-alkoxy-Neu5Ac). This method can be readily and easily scaled up. According to the process, N-acetylneuraminic acid is alkylated (preferably methylated) by a two-step process at C-1 and C-2 to provide an alkyl ester alkyl ketoside (preferably a methyl ester methyl ketoside). The vicinal hydroxyl groups located at C-8 and C-9 of the alkyl ester alkyl ketoside are then protected by the formation of a ketal. The ketal is formed through the treatment of the alkyl ester alkyl ketoside with acetone and a catalyst. The protected alkyl ester alkyl ketoside is then alkylated at the C-4 position whereby the hydrogen on the C-4 hydroxy group is replaced by an alkyl group to form an alkoxy group at the C-4 position° The ketal group formed at C-8 and C-9 is removed by treatment with acetic acid. Final deprotection is accomplished by removing the alkyl groups at C-1 and C-2 by alkaline treatment and subsequent acid hydrolysis.

It is an object of this invention to provide a synthesis method for substrates useful in diagnostic methods for the detection of viruses. Another object of this invention is to provide a practical, convenient, and cost effective method for preparing 4-alkoxy-Neu5Ac. Another object of this invention is to provide a method for the synthesis of 4-alkoxy-Neu5Ac which can be readily scaled-up. Another object of this invention is to provide a method for the synthesis of 4-alkoxy-N-Neu5Ac comprising alkylating a protected alkyl ester alkyl ketoside at C-4 to form an alkoxy group at C-4.

Still another object of this invention is to provide a process for the synthesis of 4-alkoxy-N-acetylneuraminic acid, said process comprising:

(a) protecting the vicinal hydroxyl groups at C-8 and C-9 in a N-acetylneuraminic acid derivative having an alkyl ester at C-1 and an alkyl ketoside at C-2 by forming a ketal in the presence of an acid catalyst;

(b) alkylating the protected derivative from step (a) at C-4 to form an alkoxy group at C-4; and (c) deprotecting the alkylated, protected derivative from step (b) by removing the ketal at C-8 and C-9 and by removing the alkyl groups at C-1 and C-2 to form the 4-alkoxy-N-acetylneuraminic acid.

Still another object of this invention is to provide a process for the synthesis of 4-alkoxy-N-acetylneuraminic acid, said process comprising:

(a) alkylating the carboxylic acid group at C-1 and the hydroxyl group at C-2 of N-acetylneuraminic acid to form an alkyl ester alkyl ketoside of N-acetylneuraminic acid;

(b) protecting the vicinal hydroxyl groups at C-8 and C-9 in the alkyl ester alkyl ketoside by forming a ketal in the presence of an acid catalyst selected from the group consisting of p-toluenesulfonic acid, salts of p-toluenesulfonic acid, $ZnCl_2$, and $FeCl_3$;

(c) alkylating the hydroxyl group at C-4 in the protected alkyl ester alkyl ketoside of step (b) to form an alkoxy group at C-4; and (d) removing the ketal group formed at C-8 and C-9 and removing the alkyl groups at C-1 and C-2 in the product from step (c) to provide the 4-alkoxy-N-acetylneuraminic acid.

Still another object of this invention is to provide a process for the synthesis of 4-alkoxy-N-acetylneuraminic acid wherein said 4-alkoxy group is 4-methoxy or 4-ethoxy, said process comprising:

(a) methylating the carboxylic acid group at C-1 of N-acetylneuraminic acid in the presence of a catalyst selected from the group consisting of trifluoroacetic acid and cation exchange resins to form a methyl ester of N-acetylneuraminic acid;

(b) methylating the hydroxyl group at C-2 of the methyl ester of N-acetylneuraminic acid in the presence of an effective amount of acetyl chloride to form a methyl ester methyl ketoside of N-acetylneuraminic acid;

(c) protecting the vicinal hydroxyl groups at C-8 and C-9 of the methyl ester methyl ketoside by forming a ketal in the presence of an acid catalyst selected from the group consisting of p-toluenesulfonic acid, salts of p-toluenesulfonic acid, $ZnCl_2$, and $FeCl_3$;

(d) alkylating the hydroxyl group at C-4 of the protected methyl ester methyl ketoside to form a methoxy or ethoxy group at C-4, wherein the alkylation is conducted at a temperature of from about 0° C. to about 30° C. for about 10 minutes to about 24 hours; and (e) removing the ketal group formed at C-8 and C-9 by treatment with acetic acid, and removing the methyl groups at C-1 and C-2 by alkaline treatment and subsequent acid hydrolysis to provide 4-alkoxy-N-acetylneuraminic acid wherein said 4-alkoxy group is 4-methoxy or 4-ethoxy.

Other objects, advantages, features and characteristics of the present invention will become more apparent upon consideration of the following description and the appended claims.

DETAILED DESCRIPTION OF THE INVENTION

The process described herein provides a method to specifically alkylate the C-4 hydroxyl group of N-acetylneuraminic acid (Neu5Ac) to form a 4-alkoxy group. Specifically, the process described herein provides an improved method to prepare a 4-alkoxy-N-acetylneuraminic acid of general formula

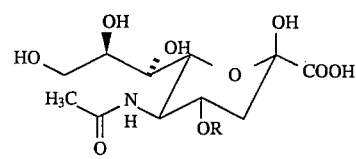

where R is an alkyl group containing from 1 to 6 carbon atoms. The higher alkyl groups (i.e., when R contains 3 to 6 carbon atoms) can include linear, branched, and cyclic isomers. Preferably R is an alkyl group containing 1 to 4 carbon atoms; more preferably R is an alkyl group containing 1 or 2 carbons atoms; even more preferably R is methyl. Specificity in regard to the alkoxy group at C-4 is effected by protecting and subsequently deprotecting reactive groups in the Neu5Ac molecule. Further reaction specificity is effected through the control of reaction conditions. The reaction scheme described herein provides a simple, cost effective process which provides high yields of 4-alkoxy-Neu5Ac. This procedure can easily be scaled up to provide commercial quantities of 4-alkoxy-Neu5Ac at reasonable costs. The general synthesis of the 4-alkoxy-Neu5Ac, using the generally preferred reactants as described in more detail below, is illustrated in the reaction scheme below (where R is an alkyl group containing 1 to 6 carbon atoms).

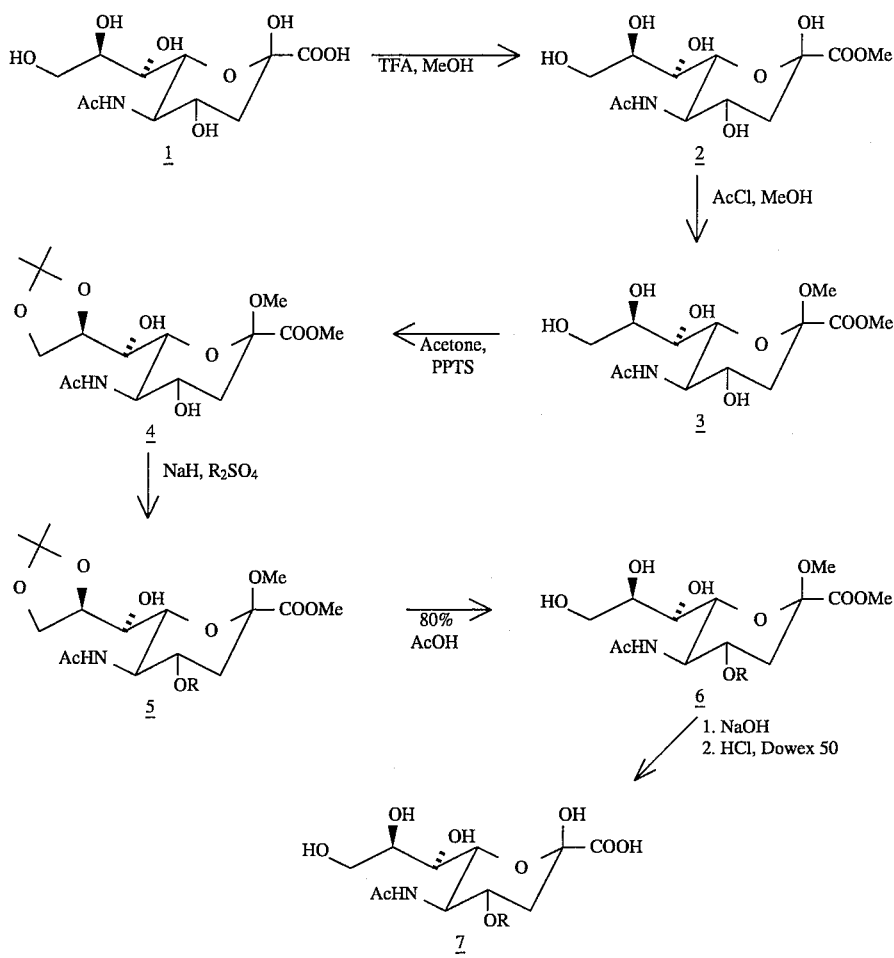

The starting material, Neu5Ac (1), is commercially available (MediHerb Inc., 4540 S. Navajo #1, Englewood, Colo. 80110). It may also be synthesized enzymatically from N-acetyl-D-mannosamine and pyruvic acid using the procedure described by Kim et al., *J. Am. Chem. Soc.*, 110 (1988) 6481, and illustrated by the following equation:

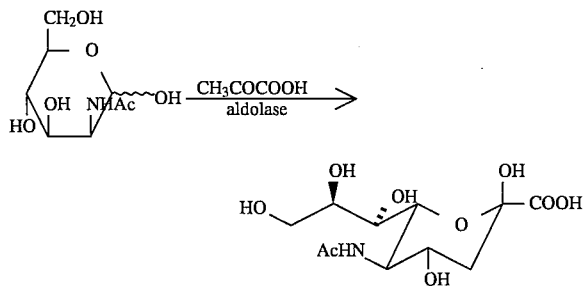

The enzymatic reaction can be monitored by thin layer chromatography (TLC) and the product can be purified by ion exchange chromatography.

In the present invention, the carboxylate group at C-1 and the hydroxyl group at C-2 of Neu5Ac are first protected by alkylation. Alkylation of the groups at C-1 and C-2 is preferably methylation, but may also include ethylation, propylation, and butylation. In a preferred embodiment of the invention, Neu5Ac is converted into the alkyl ester alkyl ketoside in a two-step process. Even more preferably, this two-step alkylation involves a two-step preferred methylation process to form the methyl ester methyl ketoside (3). In this first methylation step, the C-1 carboxyl group is methylated with anhydrous methanol in the presence of an acid catalyst. Suitable catalysts include trifluoroacetic acid (TFA) and cation exchange resins. Suitable cation exchange resins include Dowex 50 ($H^+$), Amberlyst 15 ($H^+$), and the like. (The use of methanolic acetyl chloride in the first methylation step is generally not recommended as it may lead to unwanted byproducts such as the acyl chloride derivative). In the second preferred methylation step, the C-2 hydroxyl group is methylated by utilizing methanolic acetyl chloride. The use of methanolic acetyl chloride in the second step reduces the undesired hydrolysis of the methyl ketoside which generally occurs in prior art methods using Dowex 50 ($H^+$) resin to effect this methylation.

The two-step alkylation gives better yields, since the work-up after the first step allows for removal of water which is generated during alkylation. The presence of water is undesirable since it promotes the cleavage of the newly formed glycosidic bond. In the present invention, when acetyl chloride is used in the second step, water formed during methylation reacts with the acetyl chloride to produce acetic acid and anhydrous HCl, thereby reducing or eliminating hydrolysis. The elimination of Dowex resin from the second alkylation step reduces processing time and cost, as well as improves the yield, since drying Dowex resin is a lengthy and difficult process which can decrease the alkylation yield if done improperly.

In the next step of the process, the vicinal hydroxyl groups at C-8 and C-9 of the methyl ester methyl ketoside (3) are protected by the formation of a ketal (4). The methyl ester methyl ketoside is treated with effective amounts of acetone and an acid catalyst to form the ketal. Suitable acid catalysts include p-toluenesulfonic acid, salts of p-toluenesulfonic acid such as the pyridinium salt (PPTS) and other salts, $ZnCl_2$, $FeCl_3$ and the like. The preferred acid catalyst is the non-hygroscopic pyridinium salt of p-toluenesulfonic acid.

The protected methyl ester methyl ketoside (4) is then alkylated at C-4 to form intermediate (5) containing a alkoxy group at the 4-position. Alkylation of the hydroxyl group at C-4 may be methylation, ethylation, propylation, butylation, pentylation, or hexylation, whereby the hydroxy group at C-4 is converted to a RO— group where R is an alkyl radical containing 1 to 6 carbon atoms. Preferably, the alkylation at C-4 is methylation, ethylation, propylation, or butylation. More preferably, the alkylation at C-4 is methylation or ethylation, whereby a 4-methoxy or a 4-ethoxy derivative is obtained. Even more preferably, the alkylation at C-4 is methylation, whereby a 4-methoxy derivative is obtained. Introduction of higher alkyl groups at the C-4 position is generally slower than methylation and the yields are somewhat lower. Furthermore, chromogenic substrates with higher alkyl groups tend to be less susceptible to enzymatic cleavage than 4-methoxy-Neu5Ac, thereby resulting in less sensitive assays. Nonetheless, for some specific applications and assays, such higher alkyl groups at C-4 may be useful and even preferred.

Alkylation at the more sterically hindered free hydroxyl group at C-7 can essentially be prevented and alkylation at the N-acetyl group at C-5 can be minimized by controlling the reaction conditions as described immediately hereafter. In accordance with the process, intermediate (4) is treated with from about 1.2 to about 1.4 molar equivalents of an alkylating agent in about an 80% sodium hydride. The alkylating agent is selected from the group consisting of dimethyl sulfate, diethyl sulfate, dipropyl sulfates, dibutyl sulfates, dipentyl sulfates, and dihexyl sulfates. The reaction is generally conducted at a temperature of from about 0° C. to about 30° C. for about 10 minutes to about 48 hours. Preferably the reaction temperature is in the range of about 0° C. to about 22° C. Longer reaction times are generally preferred when forming the higher alkoxy groups at the 4-position. In a preferred embodiment of the invention, a methylation reaction to form a methoxy group at C-4 is conducted at a temperature of from about 0° C. to about 30° C., more preferably from about 0° C. to about 22° C., for about 10 minutes to about 30 minutes. In another preferred embodiment of the invention, an ethylation reaction to form an ethoxy group at C-4 is conducted at a temperature of from about 0° C. to about 30° C, more preferably from about 0° C. to about 22° C, for about 1 hour to about 24 hours. Yields of the 4-methoxy and 4-ethoxy derivatives (5) greater than about 60% and 40%, respectively, can be obtained after purification by column chromatography.

Removal of the ketal group from (5) is achieved by treatment with about 80% acetic acid. Acetic acid hydrolysis can also result in partial acetylation at the C-9 hydroxyl group. Hence, the hydrolysis product can be treated with sodium methoxide to remove any acetate groups on C-9. Final deprotection of (6) is performed by alkaline treatment and subsequent acid hydrolysis to give the final 4-alkoxy-Neu5Ac product (7).

4-Alkoxy-Neu5Ac can be further utilized through coupling to any suitable marker group, including for example, a chromogenic or fluorometric marker group. The preferred marker group is a chromogenic group, including, for example, 4-chloro-1-naphthol, 6-bromo-1-naphthol, and 5-bromo-4-chloro-indole. Chromogenic modified 4-alkoxy-Neu5Ac can be incorporated into a neuraminidase assay useful for detecting viral neuraminidase activity in clinical samples or specimens. Methods for synthesizing and using such 4-position modified chromogenic N-acetylneuraminic acid substrates in viral assays are described in PCT Publication Number WO 91/09972; Yolken et al., *J. Infectious Diseases*, 142 (1980) 516–523; and Pachucki et al., *J. Clinical Microbiology*, 26 (1988) 2664-2666, each of which are incorporated herein by reference. Of course, the present 4-alkoxy-N-acetylneuraminic acids can be used to form other chromogenic- and fluorometric-containing derivatives and can be used in other viral assays.

The following examples illustrate methods for carrying out the invention and should be understood to be illustrative of, but not limiting upon, the scope of the invention which is defined in the appended claims.

EXAMPLE I

4-Methoxy-N-Acetylneuraminic Acid

The synthesis of 4-methoxy-Neu5Ac is set forth in the reaction scheme below and described as follows. Compound 2 was obtained by the esterification of N-acetylneuraminic acid (1, MediHerb, Englewood, Colo.) according to a published procedure (Baumberger et al., *Helv. Chim. Acta* 69 (1986) 1927).

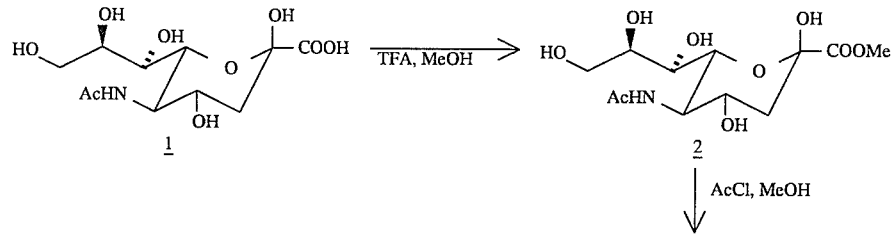

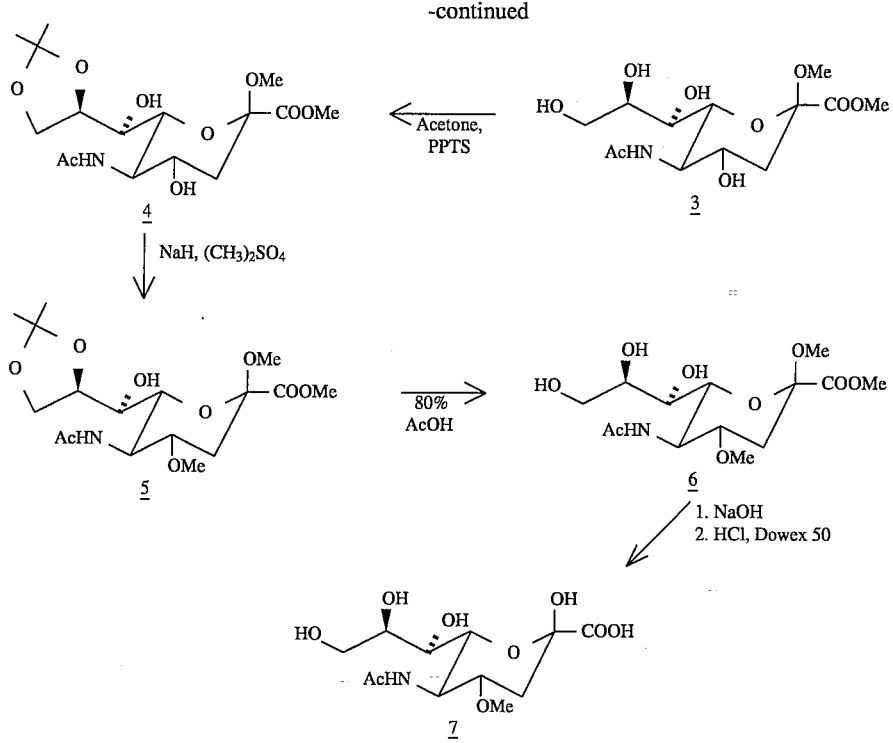

To a cold (ice-bath) solution of 2 (10 g) in methanol (200 ml) was added acetyl chloride (10 ml), and the mixture was stirred for 3 hours at 70° C. The mixture was evaporated to dryness and the residue was dried under vacuum to give crude methyl ester methyl ketoside (3). The crude 3 was converted into the acetal (4) by a known procedure (Hagedorn et al. *Helv. Chim. Acta* 69 (1986) 2127). To a solution of 3 in acetone (300 ml) was added pyridinium p-toluenesulfonate (50 mg). The mixture was stirred at room temperature for one hour. The mixture was then neutralized with Dowex 1 (OH), and the resin was filtered off and washed with acetone. The filtrate was evaporated to dryness and the residue was purified on a silica gel column. Elution with methylene chloride:methanol (15:1) removed most of the byproducts. Continued elution with methylene chloride:methanol (9:1) afforded the pure methyl 5-acetamido-3, 5-dideoxy-8,9-O-isopropylidene- 4-methoxy-$\beta$-D-glycero-D-galacto-2-nonulopyranosidonic acid methyl ester (4, 5.19 g, 45%).

To a cold (ice bath) solution of 4 (1.7 g) in acetonitrile (15 ml) was added (under nitrogen) sodium hydride (80% dispersion, 245 mg). The mixture was stirred for 15 minutes in an ice bath (under nitrogen) before adding dimethyl sulfate (0.8 ml). Stirring in the ice bath was continued for an additional 20 minutes. The mixture was filtered through celite, and the filtrate was evaporated to dryness. The residue was purified on a silica gel column (80 g) and the pure product (5) was eluted with methylene chloride:methanol (25:1). The yield of 5 was 1.22 grams (69%). Compound 5 (1.22 g) was treated with 80% aqueous acetic acid (15 ml) at 85° C. for 1 hour. The acetic acid was removed by evaporation and co-evaporation with water. The residue was treated with M sodium methoxide solution (2.2 ml) in methanol (10 ml) at room temperature for 1 hour. The pH of the mixture was adjusted to about pH 7 with Dowex 50 ($H^+$) resin, the resin removed by filtration, and the filtrate evaporated. The residue was purified on a silica gel column and the product was eluted with methylene chloride-methanol (5:1 by volume). The yield of 6 was 0.87 g (80%).

Compound 6 (0.87 g) was treated with M sodium hydroxide solution (3.0 ml) in water (3.5 ml) and ethyl alcohol (3.5 ml) at room temperature for 1 hour. The mixture was neutralized with Dowex 50 ($H^+$) resin, filtered to remove the resin, and the filtrate evaporated. The residue was treated with Dowex 50 ($H^+$) (1.5 g) and 0.025M hydrochloric acid at 105° C. for 3 hours. The resin was removed by filtration and the filtrate was evaporated to dryness. The residue was dried to give the product 7 (0.71 g, 88%). The structure of 7 was confirmed by proton and carbon-13 NMR spectroscopy.

EXAMPLE II

4-Ethoxy-N-Acetylneuraminic Acid

The synthesis of 4-ethoxy-Neu5Ac is set forth in the reaction scheme below and described herein. Compounds 1 through 4 were synthesized according to the procedures set forth in Example I.

To a solution of methyl 5-acetamido-8,9-O-isopropylidene- 3,5-dideoxy-$\beta$-D-glycero-D-galacto-2-nonulopyranosidonic acid methyl ester (4, 1.69 g) in methylene chloride (10 ml) (maintained under nitrogen at 0° C.) was added 80% sodium hydride (220 mg) and the mixture was stirred for 10 minutes. Diethyl sulfate (2.5 ml) was added, and the mixture was stirred for 15 minutes in an ice-bath, and for an additional 17 hours at room temperature (under nitrogen). The mixture was filtered through celite and the filtrate was evaporated. The crude residue was purified on silica gel (60 g) and the product was eluted with methylene chloride-methanol (25:1 by volume). The yield of 5 was 0.76 g (42%). The structure of the product was confirmed by NMR spectroscopy.

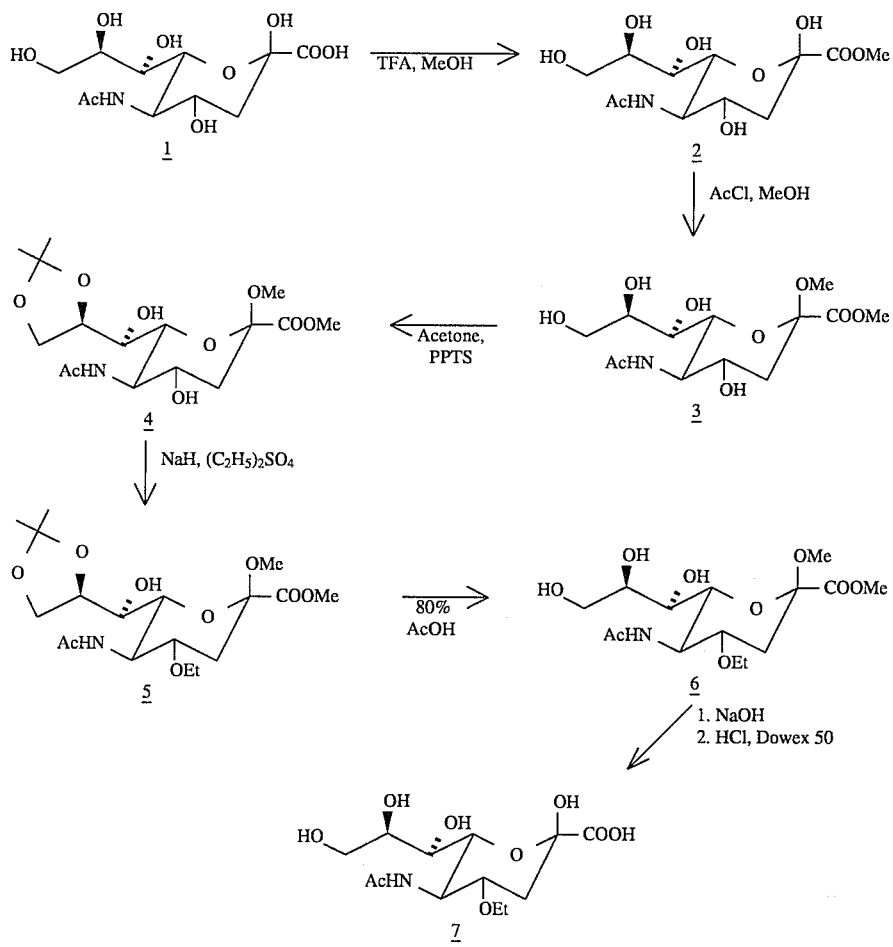

Compound 5 (686 mg) was treated with 80% aqueous acetic acid (10 ml) at 90° C. for 1 hour. The mixture was evaporated and the residue was treated with M sodium methoxide solution (1.6 ml) in methanol (5 ml). The mixture was stirred for 1 hour at room temperature, neutralized with Dowex 50 (H$^+$), filtered, and then evaporated. The residue was purified on silica gel (30 g). Elution with methylene chloride-methanol (5:1 by volume) removed a fast-moving by-product. Continued elution with the same solvent system gave compound 6 (450 mg, 73%). Compound 6 (450 mg) was treated with M sodium hydroxide solution (1 ml) in a mixture of ethyl alcohol (5 ml) and water (5 ml) at room temperature for 1 hour. The mixture was neutralized with Dowex 50 (H$^+$) and evaporated. The residue was treated with Dowex 50 (H$^+$) (900 mg) in 0.025M hydrochloric acid at 90° C. for 4 hours, and evaporated. The residue was dried to give compound 7 (333 mg, 80%). The structure of the product was confirmed by NMR spectroscopy.

Numerous modifications and variations in practice of the invention are expected to occur to those skilled in the art upon consideration of the foregoing detailed description of the invention. Consequently, such modifications and variations are intended to be included within the scope of the following claims.

That which is claimed is:

1. A process for the synthesis of 4-alkoxy-N-acetylneuraminic acid, said process comprising:
   (a) protecting the vicinal hydroxyl groups at C-8 and C-9 in a N-acetylneuraminic acid derivative having an alkyl ester at C-1 and an alkyl ketoside at C-2 by forming a ketal in the presence of an acid catalyst;
   (b) alkylating the protected derivative from step (a) at C-4 to form an alkoxy group at C-4; and
   (c) deprotecting the alkylated, protected derivative from step (b) by removing the ketal at C-8 and C-9 and by removing the alkyl groups at C-1 and C-2 to form the 4-alkoxy-N-acetylneuraminic acid.

2. A process according to claim 1, wherein the acid catalyst used to form the ketal is selected from the group consisting of p-toluenesulfonic acid, salts of p-toluenesulfonic acids ZnCl$_2$ and FeCl$_3$.

3. A process according to claim 2, wherein the acid catalyst is a pyridinium salt of p-toluenesulfonic acid.

4. A process according to claim 1, wherein the alkylation at C-4 forms an alkoxy group at C-4 of the formula RO- where R is an alkyl group containing 1 to 6 carbon atoms.

5. A process according to claim 4, wherein the alkylation is conducted with an alkylating agent selected from the group consisting of dimethyl sulfate, diethyl sulfate, dipropyl sulfates, dibutyl sulfates, dipentyl sulfates, and dihexyl sulfates.

6. A process according to claim 4, wherein the alkylation is conducted at a temperature of from about 0° C. to about 30° C. for about 10 minutes to about 48 hours.

7. A process according to claim 6, wherein the alkylation is methylation which is conducted at a temperature of from about 0° C. to about 22° C. for about 10 minutes to about 30 minutes.

8. A process according to claim 1, wherein the ketal group at C-8 and C-9 is removed by treatment with acetic acid.

9. A process according to claim 1, wherein the alkyl groups at C-1 and C-2 are removed by alkaline treatment and subsequent acid hydrolysis.

10. A process for the synthesis of 4-alkoxy-N-acetylneuraminic acid, said process comprising:

(a) alkylating the carboxylic acid group at C-1 and the hydroxyl group at C-2 of N-acetylneuraminic acid to form an alkyl ester alkyl ketoside of N-acetylneuraminic acid;

(b) protecting the vicinal hydroxyl groups at C-8 and C-9 in the alkyl ester alkyl ketoside by forming a ketal in the presence of an acid catalyst selected from the group consisting of p-toluenesulfonic acid, salts of p-toluenesulfonic acid, $ZnCl_2$, and $FeCl_3$;

(c) alkylating the hydroxyl group at C-4 in the protected alkyl ester alkyl ketoside of step (b) to form an alkoxy group at C-4; and (d) removing the ketal group formed at C-8 and C-9 and removing the alkyl groups at C-1 and C-2 in the product from step (c) to provide the 4-alkoxy-N-acetylneuraminic acid.

11. A process according to claim 10, wherein the carboxylic acid group at C-1 is alkylated in the presence of a catalyst.

12. A process according to claim 11, wherein the catalyst is selected from the group consisting of trifluoroacetic acid and cation exchange resins.

13. A process according to claim 10, wherein the hydroxyl group at C-2 is alkylated in the presence of an effective amount of acetyl chloride.

14. A process according to claim 10, wherein the acid catalyst is a pyridinium salt of p-toluenesulfonic acid.

15. A process according to claim 10, wherein the hydroxy group at C-4 is alkylated to form an alkoxy group of formula RO— where R is an alkyl group containing 1 to 6 carbon atoms.

16. A process according to claim 15, wherein the alkylation at C-4 is conducted with an alkylating agent selected from the group consisting of dimethyl sulfate, diethyl sulfate, dipropyl sulfates, dibutyl sulfates, dipentyl sulfates, and dihexyl sulfates.

17. A process according to claim 16, wherein the alkylation at C-4 is conducted at a temperature of from about 0° C. to about 30° C. for about 10 minutes to about 48 hours.

18. A process according to claim 17, wherein the alkoxy group at C-4 is methoxy and the alkylation at C-4 is conducted at a temperature of from about 0° C. to about 22° C. for about 10 to about 30 minutes.

19. A process according to claim 10, wherein the ketal group at C-8 and C-9 is removed by treatment with acetic acid.

20. A process according to claim 10, wherein the alkyl groups at C-1 and C-2 are removed by alkaline treatment and subsequent acid hydrolysis.

21. A process for the synthesis of 4-alkoxy-N-acetylneuraminic acid wherein said 4-alkoxy group is 4-methoxy or 4-ethoxy, said process comprising:

(a) methylating the carboxylic acid group at C-1 of N-acetylneuraminic acid in the presence of a catalyst selected from the group consisting of trifluoroacetic acid and cation exchange resins to form a methyl ester of N-acetylneuraminic acid;

(b) methylating the hydroxyl group at C-2 of the methyl ester of N-acetylneuraminic acid in the presence of an effective amount of acetyl chloride to form a methyl ester methyl ketoside of N-acetylneuraminic acid;

(c) protecting the vicinal hydroxyl groups at C-8 and C-9 of the methyl ester methyl ketoside by forming a ketal in the presence of an acid catalyst selected from the group consisting of p-toluenesulfonic acid, salts of p-toluenesulfonic acid, $ZnCl_2$, and $FeCl_3$;

(d) alkylating the hydroxyl group at C-4 of the protected methyl ester methyl ketoside to form a methoxy or ethoxy group at C-4, wherein the alkylation is conducted at a temperature of from about 0° C. to about 30° C. for about 10 minutes to about 24 hours; and (e) removing the ketal group formed at C-8 and C-9 by treatment with acetic acid, and removing the methyl groups at C-1 and C-2 by alkaline treatment and subsequent acid hydrolysis to provide 4-alkoxy-N-acetylneuraminic acid wherein said 4-alkoxy group is 4-methoxy or 4-ethoxy.

22. A process as defined in claim 21, wherein the 4-alkoxy group is methoxy and the alkylation of step (d) is conducted at a temperature of from about 0° C. to about 22° C. for about 10 minutes to about 30 minutes.

23. A process as defined in claim 21, wherein the 4-alkoxy group is ethoxy and the alkylation of step (d) is conducted at a temperature of from about 0° C. to about 22° C. for about 1 hour to about 24 hours.

* * * * *